United States Patent
Stuck et al.

(10) Patent No.: US 6,927,312 B2
(45) Date of Patent: Aug. 9, 2005

(54) METHOD OF REMOVING WATER FROM HYDROFLUOROCARBON MANUFACTURING PROCESSES

(75) Inventors: Jason T. Stuck, Mountain View, CA (US); Hsueh Sung Tung, Getzville, NY (US); Michael Van Der Puy, Amherst, NY (US); Timothy R. Demmin, Grand Island, NY (US); Franklin S. Wong, Orchard Park, NY (US); Andrew J. Poss, Kenmore, NY (US); Matthew H. Luly, Hamburg, NY (US)

(73) Assignee: Honeywell International Inc., Morristown, NJ (US)

( * ) Notice: Subject to any disclaimer, the term of this patent is extended or adjusted under 35 U.S.C. 154(b) by 69 days.

(21) Appl. No.: 10/706,250

(22) Filed: Nov. 12, 2003

(65) Prior Publication Data

US 2005/0101809 A1   May 12, 2005

(51) Int. Cl.⁷ ............................................. C07C 17/00
(52) U.S. Cl. ..................... 570/164; 570/168; 570/169; 570/177
(58) Field of Search ............................... 570/164, 168, 570/169, 177

(56) References Cited

U.S. PATENT DOCUMENTS

| | | | |
|---|---|---|---|
| 5,334,784 A | 8/1994 | Blake et al. | 570/165 |
| 5,723,702 A | 3/1998 | Kwon et al. | 570/177 |
| 6,101,818 A | 8/2000 | Thomas et al. | 62/85 |
| 6,103,944 A | 8/2000 | Blake et al. | 570/165 |
| 6,111,151 A | 8/2000 | Ewing et al. | 570/177 |
| 6,787,678 B1 * | 9/2004 | Tung et al. | 570/177 |

* cited by examiner

*Primary Examiner*—Johann Richter
*Assistant Examiner*—Sikarl A. Witherspoon
(74) *Attorney, Agent, or Firm*—Colleen D. Szuch

(57) ABSTRACT

Disclosed are improved fluorination processes and fluorine-containing compositions which involve introducing to one or more fluorination process compositions a water reactive agent in an amount and under conditions effective to decrease the amount of water in that composition. The water reactive agent is preferably introduced to the fluorination reaction process at a location proximate to the site of the fluorination reaction, or upstream of the fluorination reaction, in amounts and under conditions effective to produce a relatively lower concentration of water in the composition, and preferably throughout the fluorination process.

23 Claims, No Drawings

METHOD OF REMOVING WATER FROM HYDROFLUOROCARBON MANUFACTURING PROCESSES

FIELD OF THE INVENTION

This invention relates to processes for the production of fluorinated organic compounds. More particularly, the present invention relates methods for producing fluorine-containing compositions containing advantageously low levels of water.

BACKGROUND OF THE INVENTION

There are numerous processes directed to the manufacture of fluorinated organic compounds and to compositions containing such compounds. Many of these processes involve the reaction of an organic compound, such as a chloroalkane or chloroalkene, with hydrogen fluoride (HF) in the presence of a fluorination catalyst. In several of these processes, water is present in one or more of the reaction product streams containing the desired fluorinated organic compound. This water may originate as an impurity in the reactants or other starting materials. The water also may be formed as a byproduct from the reaction process, including reaction of HF with the catalyst, and/or as a product of the catalyst regeneration process.

It has been recognized that mixtures of water and hydrogen fluoride are especially corrosive, and that this combination is both difficult and expensive to handle. As a result, it is typically desirable to remove water from those portions of the fluorination processes where it is exposed to HF, including in product streams, byproduct streams, reactant streams, and recycle streams. Moreover, water which is present in the fluorination process, even at low levels, may act as a catalyst poison, thereby having deleterious effects on the effectiveness, efficiency, selectivity and/or yield of the fluorination reaction.

Several methods of removing or reducing the amount of water from fluorination process streams have previously been proposed. For example, U.S. Pat. No. 5,334,784 (Blake, et al.) and U.S. Pat. No. 6,103,944 (Blake, et al.), suggest distillation as a method for physically removing water from a fluorination process stream. U.S. Pat. No. 6,111,151 (Ewing, et al.) discloses phase separation as an alternative method of physically removing undesirable water from the process stream. In addition, drying agents such as sodium polyacrylate (U.S. Pat. No. 6,101,818, Thomas, et al.) and calcium chloride (U.S. Pat. No. 5,723,702, Kwon, et al.) have also been suggested as a means to absorb water from a process stream. While Blake, Ewing, and others in the field have attempted to remove water from the reaction product by using equipment and methods downstream of the fluorination reactor, such as those described above, these processes are inherently expensive. Moreover, known absorbents that are compatible with the fluorination reaction are not selective for water and therefore cannot generally be used to advantage during the fluorination process. Each of the aforementioned methods also pose a further disadvantage in that they can only remove water downstream of the process reaction, and therefore they are not effective for the removal of water at the reaction site and cannot prevent catalyst poisoning.

Process streams downstream of the fluorination reaction typically contain unreacted organic materials and unreacted HF in addition to the desired fluorinated compounds. To increase product yield, it is common to separate the unreacted starting components from the product stream and to recycle HF and/or the under fluorinated components back to the reaction step. Because recycling tends to increase the concentration of water present during the fluorination reaction, it is advantageous to remove any water from the product stream prior to recycling.

SUMMARY OF THE INVENTION

The present inventors have come to appreciate a need in the art for an improved fluorination process and for improved fluorine-containing compositions preferably fluorine substituted organic molecules having from about 2 to about 5 carbon atoms. We have discovered that this need can be satisfied by introducing to one or more fluorination process compositions a water reactive agent in an amount and under conditions effective to decrease the amount of water in that composition. By applying this teaching, the fluorination process and the products produced thereby can be improved. Furthermore, the present inventors have recognized that water can have a deleterious effect not only on the processing of the reaction product downstream of the reactor, but also on the fluorination reaction itself. In view of this recognition, applicants have discovered a fluorination process which preferably comprises introducing to the fluorination reaction process, preferably at a location proximate to the site of the fluorination reaction and/or or upstream of the fluorination reaction, a water reactive agent in an amount and under conditions effective to produce a relatively lower concentration of water in the reaction mixture, and preferably throughout the fluorination process.

As used herein, the term "water reactive agent" refers to one or more elements and/or compounds which react either directly or indirectly through the production of intermediate compound(s), with water present at one or more locations in the fluorination process to effectively reduce the water present in the process stream or composition. As used herein, the term "fluorination process" is intended to refer to and include the fluorination reaction itself as well as upstream processing (such as preheating, catalyst treatment, and the like), and downstream processing (such as component separation and the like). Thus, the term "fluorination process" includes the location or site of the fluorination reaction and also the streams which are fed to or withdrawn from the reaction site or vessel. In preferred embodiments, the water reactive agent is reactive under conditions which exist at one or more locations in the fluorination process. In other words, the water reactive agent is preferably added to the fluorination process at one or more locations in the process without requiring any substantial alteration of the fluorination reaction conditions, and even more preferably also without requiring any substantial alteration of the upstream and downstream process conditions.

It is also generally preferred that present methods effectively reduce the amount of water at one or more locations in the fluorination process without introducing, directly or as a reaction product, any substantial amount of deleterious new compounds to the process. As used herein, a "deleterious compound" is one which is either not readily removed from the process or which has a negative effect on the operation of the fluorination reaction. For example, a water reactive agent which is a poison to the catalyst used in the process, or which causes the formation of a catalyst poison, would be considered a deleterious compound. A compound that is otherwise already present in the process would generally not be considered a deleterious compound. It is preferred in certain embodiments that the presence of the water reactive agent of the present invention does not cause the presence of any substantial amount a new reaction product to the fluorination process. As used herein, the term "new reaction product" refers to a compound or element that is otherwise not normally present in the fluorination reaction product stream or which would require a substantial alteration of the process to accommodate. Thus, it is generally preferred that the water reactive agent itself preferably comprises a compound, or combination of compound(s) and/or element(s) that are otherwise already present in the reaction product stream.

DETAILED DESCRIPTION PREFERRED EMBODIMENTS

In preferred embodiments, particularly those embodiments directed to the production of HFCs having from two to about five carbon atoms, such as for example pentafluoroethane (HFC-125) and tetrafluoroethane (HFC-134), the water reactive agent comprises chlorine substituted vinyl compounds, such as chlorine substituted ethylene, and in particular trichloroethylene (TCE). The use of such a water reactive agent is highly preferred for use in processes in which the fluorination reaction is based on the fluorination of reactive organic compounds containing a chlorine substituted vinyl moiety, more preferably at least a dichlorine substituted vinyl moiety, and even more preferably at least a trichlorine substituted vinyl moiety. For example, the present invention is especially well adapted to produce exceptional results when used in connection with the fluorination of perchloroethylene (PCE). In optional but preferred embodiments, the water reactive agent further comprises oxygen.

It is contemplated that, in view of the teachings contained herein, those skilled in the art will be able to identify without undue experimentation numerous water reactive agents that are adaptable for use in connection with the present methods, and all such reactive agents are within the broad scope hereof. In preferred embodiments, particularly embodiments in which TCE is produced in the fluorination reaction as a byproduct, the water reactive agent consists essentially of TCE and oxygen, and the methods preferably comprise the step of introducing the water reactive agent into the fluorination process at about the site of the fluorination reaction, and even more preferably into a reaction mixture contained in a reaction vessel. It will of course be appreciated by those skilled in the art that the various components of the water reactive agent need not be introduced together or at the same time or in the same manner to the fluorination process. The only requirement in this regard is that when multi-component water reactive agents are used, they are introduced into the process such that they can ultimately cooperate to react excess water out of the system, most preferably without introducing a substantial amount of any new reaction product to the system. It is believed that this process is effective for reducing the amount of water present in the process independent of the origin of the water. Because the preferred water removal agents and associated reaction products may be chemical components already found in and/or are readily removed from a fluorocarbon manufacturing process, no unusual contaminants are introduced. In preferred embodiments, the processes of the present invention produce a product stream which does not include a substantial amount of water, and which even more preferably is substantially water-free.

It should also be appreciated that the step of introducing the water reactive agent to the process, unless indicted otherwise herein, should be construed broadly to include, for example, the step of introducing to the process a precursor to the water reactive agent which is converted during to the fluorination process to the water reactive agent. For example, a polyhaloepoxide, such as trichloroethylene epoxide may in certain embodiments be introduced into the process under conditions which result in the formation of a preferred water reactive agent comprising TCE.

The preferred embodiments of this invention thus provide methods for reducing the concentration of water in a reaction product stream produced by a fluorination reaction process by introducing into the fluorination reaction mixture a water reactive agent, preferably trichloroethylene (TCE) or TCE in combination with oxygen, in amounts sufficient and under conditions effective to substantially reduce the water in the composition of the reaction mixture. In preferred embodiments the water reactive agent is introduced to the reaction mixture as a separate stream or as a component of one or more of the feed streams to the reactor. Those skilled in the art will appreciate that the water reactive agent may alternatively or additionally be introduced into one or more of the effluent streams from the reactor, although such embodiments would generally be considered less preferred.

According to a first aspect of the invention, methods are provided for reducing the amount of water in a fluorination process stream that comprises hydrogen fluoride (HF), reactive organic compounds and water in the form of moisture or otherwise. The process stream may also contain recycled byproducts of the fluorination reaction and possibly fluorinated organic compounds. Trichloroethylene (TCE) or TCE and oxygen are preferably introduced into the reactor feed steam containing the organic reactants, preferably without substantial alteration of the conditions otherwise existing in the process stream and without substantial alteration of the reaction conditions.

Although applicants do not wish to necessarily be bound by or limited to any particular theory of operation, it is believed that the preferred reactive agents of the present invention, particularly TCE when combined with oxygen in the presence of an acid under fluorination reaction conditions, form or include a carbocation, and that subsequent hydrolysis of this carbocation eliminates water molecules from the fluorination process. In preferred embodiments, therefore, the reactive agent is a compound or radical that includes and/or is converted during the fluorination process to an intermediate, and/or a compound and/or a radical, particularly one that comprises a carbocation. This intermediate, compound or radical is subsequently reduced in the presence of water through a hydrolysis reaction. A substantial portion of the water is thereby removed form the process stream. One possible reaction mechanism by which the water (referred to as "process" water below) is removed is believed to involve a mechanism in which TCE reacts with oxygen to form trichloroethylene oxide as the first step. In the second step, acids present facilitate the reaction of water with trichloroethylene oxide. The products of the second step decompose under the reaction conditions to form single-carbon species such as CO, CO2, and chloromethanes. In another possible reaction mechanism, TCE proceeds through direction with water, preferably in the presence of acid. These two potential schemes are illustrated as follows:

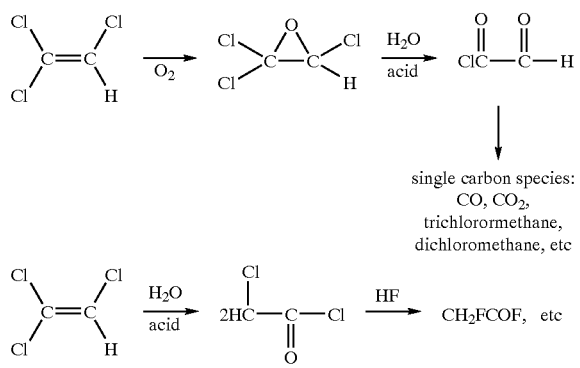

As can be seen from the above, the postulated possible reaction mechanisms all result in the water reactive agent TCE, through an epoxide intermediate, producing a series of relatively unstable compounds that convert under the applicable process conditions to single carbon species that are not deleterious to the process. Furthermore, it is believed that one of the more dominant reaction schemes, as shown above, involves the consumption of water, thereby effectively removing water from the system.

Preferably, the reaction mechanism(s) by which the water is removed occur within a temperature range from about 100° C. (212° F.) to about 540° C. (1004° F.) and a pressure of from about 0 psia to about 500 psia. More preferably, these reactions occur within a temperature range from about 200° C. (392° F.) to about 425° C. (800° F.), and even more preferably at about 260° C. (500° F.) to about 370° C. (700° F.). The preferred concentration of TCE is from about 0.01 to about 95 mole percent, based on the total organics present in the process where it is added. More preferably, the concentration of TCE is from about 0.05 to about 50 mole percent based on the organics in the reaction medium. Even more preferably, the concentration of TCE is from 0.1 to about 20 mole percent based on the total organics. In addition, the preferred concentration of oxygen is from about 0.01 to about 50 mole percent, with a more preferred concentration of from about 0.1 to about 10 mole percent, based on the total organics and oxygen in the process where it is added.

According to a second aspect of the invention, there is provided a method for creating a process stream of fluorinated organic compounds essentially free of water. This process stream is created by adding a first co-feed of TCE, and optionally but preferably a second co-feed of oxygen, to a fluorination process stream which contains more than trace amounts of water. The TCE, and preferably oxygen, react in such a process stream according to the first aspect of the invention to reduce or substantially eliminate the water from the process stream. The fluorination process, as well as the water removal method, can be carried out in a wide variety of environments and in batch, continuous, and/or semi-continuous operations. It is generally preferred, however, that the methods are carried out in continuous or semi-continuous operations. Furthermore, it is generally preferred that the water be removed at or about the time that the reactive organic compound is being fluorinated, that is, during the fluorination reaction.

The principle operation of the preferred fluorination process is reacting a fluorination agent, such hydrogen fluoride (HF), with a reactive organic compound, more preferably halogenated hydrocarbons, even more preferably chlorinated hydrocarbons (CHC's), and most preferably chlorinated alkanes and alkenes. Examples of preferable chlorinated alkanes and alkenes include, but are not limited to, dichloromethane, trichloroethane, dichloroethylene, tetrachloropropane, pentachloropropane, hexachloropropane, trichloropropylene, tetrachloropropylene, and the like. The product resulting from the preferred fluorination process of the present invention generally comprises chloroflurocarbons (CFC's), hydrofluorocarbons (HFC's), hydrochlorofluorocarbons (HCFC's) and combinations of these. As desired, more than one hydrofluorocarbon may be produced in the process by co-production with another hydrofluorocarbon.

Many suitable catalytically active compounds are well known in the art, and include various inorganic compounds, for example oxides and halides of metals such as aluminum, cobalt, manganese, iron, and chromium. A preferred embodiment of the present invention utilizes a chromium based catalyst in the fluorination process. In one embodiment of the invention in which a chromium based catalyst is used, the fluorination reaction occurs in a range of temperature from about 200° C. (392° F.) to about 400° C. (752° F.), more preferably from about 320° C. (608° F.) to about 375° C. (707° F.), and even more preferably about 350° C. (662° F.). The operating pressure is preferably from about 50 psig to about 200 psig, with about 100 psig being most preferred in certain embodiments.

The water to be removed from the process stream may be introduced from one or more sources, such as water present in one or more of the reactants, water included or otherwise present in the catalyst, water produced as a result of interaction between one or more of the reactants and the catalyst (either fresh or regenerated), water produced during conditioning/regeneration of the catalysts, or water contained in any other medium introduced in the course of the reaction. Typically, the water content of the process stream will be from about 0.05 to about 5 wt. % based on the weight of the water and HF. Usually, prior to contact with the HF, the organic starting material will exist as a gaseous product stream at a temperature above the dew point of any water existing as an impurity in the HF starting component. In many embodiments it is preferred that the water reactive agent is exposed to a fluorination process stream that is at a temperature of from 100° C. (212° F.) and 550° C. (1022° F.) in order to maximize the remove of the water.

The amount of water created as a byproduct of the fluorination process typically increases gradually as the reaction process progresses. The present invention preferably removes this water through the addition of TCE, and preferably also oxygen, as co-feeds into one or more compositions and/or process streams associated with the fluorination reaction. According to certain preferred embodiments, the water reactive agent in general, and the TCE and/or oxygen in particular, are introduced as co-feeds into the reaction mixture. This can be achieved by adding the water reactive agent to one or more of the feeds to the reaction vessel or by introducing the agent separately to the reaction vessel. In preferred embodiments, the water reactive agents, such as TCE and/or oxygen, react to form a reactant which hydrolyzes in the presence of water, thus removing the water from the process stream. For example, as organic compounds are fluorinated in the presence of a chromium based catalyst, the TCE and oxygen react to form an intermediate compound which reacts with and thereby eliminates a portion, and preferably a substantial portion, of the water from the process stream. The reacted products are preferably separated from the process stream and the unreacted products are recycled back into the fluorination reactor. The reacted products extracted from the process stream are preferably substantially free of water.

What is claimed is:

1. A method of removing water from a fluorination process comprising:
   a) providing at least one water reactive agent comprising a chlorine substituted vinyl compound having from 2 to about 5 carbon atoms;
   b) providing in said fluorination process a composition containing a reactive organic compound, a fluorination agent and water; and
   c) introducing said water reactive agent into said composition under conditions effective to substantially reduce the concentration of water in said composition.

2. A method of removing water from a fluorination process stream comprising:
   a) providing a process stream containing an organic compound, hydrogen fluoride, and water;
   b) introducing a chlorine substituted vinyl compound having from 2 to about 5 carbon atoms into said process stream;
   c) reacting said chlorine substituted vinyl compound to form an intermediate reactive with water; and
   d) removing water from the process stream by hydrolyzing said intermediate with said water.

3. The method of claim 2 wherein the intermediate compound comprises a carbocation.

4. The method of claim 2 wherein said chlorine substituted vinyl compound comprises trichloroethylene and said intermediate comprises a substituted acetaldehyde.

5. The method of claim 2 wherein said intermediate comprises trichloroethylene oxide.

6. The method of claim 2 wherein said reacting step c) comprises reacting said chlorine substituted vinyl compound in the presence of oxygen.

7. The method of claim 6 wherein said reacting step c) comprises reacting said chlorine substituted vinyl compound in the presence of oxygen to form an intermediate comprising trichloroethylene oxide.

8. The method of claim 2 wherein the temperature of said process stream is from about 100° C. to about 550° C.

9. The method of claim 2 wherein the pressure of said process stream is from about 50 psig to about 100 psig.

10. The method of claim 4 wherein said substituted acetaldehyde, comprises 2,2-dichlorohydroxyacetaldehyde.

11. The method of claim 3 wherein said carbocation has the formula $Cl_2$—$C^+$—R, wherein R is selected from the group consisting of methyl aldehyde, methyl hydroxychloride, and combinations of these.

12. A method of making fluorinated organic compounds comprising the steps of:
   a.) reacting at least one organic reactive compound under conditions effective to fluorinate said organic reactive compound to produce a reaction mixture, said reaction mixture comprising water; and
   b.) introducing into said reaction mixture a water reactive agent comprising a chlorine substituted vinyl compound having from 2 to about 5 carbon atoms, said water reactive agent being effective under the step a) fluorination conditions to remove at least a substantial portion of said water from said reaction mixture.

13. The method in claim 12 wherein said reactive organic compound is a chlorinated vinyl compound.

14. The method in claim 13 wherein said chlorinated vinyl is ethylene having at least one chlorine substituent.

15. The method in claim 14 wherein said chlorinated vinyl compound comprises trichloroethylene.

16. The method of claim 12 wherein said water reactive agent comprises from about 0.05 mole % to 50 mole % of said reaction mixture based on the total weight of the organics plus the weight of the water reactive agent.

17. The method of claim 12 wherein a substantial portion of any water present in the fluorinated organic compound product stream is removed after reacting with a compound selected from the group consisting of trichloroethylene, oxygen, an intermediary product produced by the reaction of trichloroethylene, an intermediary product produced by the reaction of trichloroethylene with oxygen in the presence of an acid, and combinations of two or more of these.

18. The method of claim 12 wherein said reaction step a) comprises reacting said reactive organic compound with hydrogen fluoride in the presence of a fluorination catalyst to form a fluorinated organic compound product stream containing a water by-product.

19. The method of claim 18 wherein said introducing step b) further comprises introducing oxygen into said reaction mixture.

20. The method of claim 18 wherein said fluorination catalyst comprises chromium.

21. The method of claim 12 wherein the fluorinated organic compound is a hydrofluorocarbon.

22. The method of claim 12 wherein the fluorinated organic compound is a hydrochlorofluorocarbon.

23. A method of removing water from a fluorination process of the type having a process stream containing a reactive organic compound, a fluorination agent and water, the method comprising introducing at least one water reactive agent comprising a chlorine substituted vinyl compound having from 2 to about 5 carbon atoms into said process stream under conditions effective to substantially reduce the concentration of water in said process.

* * * * *